United States Patent [19]  [11] 3,932,412
Simpson  [45] Jan. 13, 1976

[54] 1-(4-HYDROXYALKYLPIPERAZINO)-ISOQUINOLINE NITRATES

[75] Inventor: William R. J. Simpson, Hanover, N.J.

[73] Assignee: Sandoz, Inc., E. Hanover, N.J.

[22] Filed: Aug. 6, 1973

[21] Appl. No.: 386,084

Related U.S. Application Data

[62] Division of Ser. No. 95,989, Dec. 7, 1970, Pat. No. 3,778,440.

[52] U.S. Cl. 260/268 BQ; 260/268 TR; 260/283 R; 260/286 R; 260/289 R; 424/250
[51] Int. Cl.² .......................... C07D 295/12
[58] Field of Search .......... 260/288 R, 268 BQ

[56] References Cited
UNITED STATES PATENTS

| | | | |
|---|---|---|---|
| 3,511,836 | 5/1970 | Hess | 260/256.4 |
| 3,517,005 | 6/1970 | Cronin et al. | 260/288 R |
| 3,637,699 | 1/1972 | Gabel et al. | 260/256.4 |
| 3,637,700 | 1/1972 | Gabel et al. | 260/256.4 |
| 3,637,701 | 1/1972 | Gabel et al. | 260/256.4 |
| 3,778,440 | 12/1973 | Simpson | 260/288 R |

*Primary Examiner*—Donald G. Daus
*Assistant Examiner*—Jose Tovar
*Attorney, Agent, or Firm*—Gerald D. Sharkin; Richard E. Vila

[57] ABSTRACT

Disclosed are compounds of the class of isoquinolines substituted at the 1-position by an amino function bearing a hydroxy-alkyl nitrate moiety, e.g., 1-(5-hydroxypentyl)-amino-6,7-methylene-dioxyisoquinoline nitrate. The compounds have various pharmacological activities in animals and are useful, for example, as anti-hypertensive agents, anti-anginal agents and in the treatment of shock. Also disclosed are the corresponding hydroxy intermediates which are useful in preparation of the nitrates and also as hypotensive agents or as agents in the treatment of shock.

6 Claims, No Drawings

1-(4-HYDROXYALKYLPIPERAZINO)-ISOQUINOLINE NITRATES

This is a division of application Ser. No. 95,989 filed Dec. 7, 1970, now U.S. Pat. No. 3,778,440.

This invention relates to isoquinoline derivatives, and more particularly to isoquinolines which are substituted at the 1-position by an amino function bearing a hydroxyalkyl nitrate moiety. The invention also relates to pharmaceutical methods and compositions utilizing said compounds. The invention further relates to corresponding hydroxyalkyl substituted isoquinolines useful as intermediates in preparation of said nitrates.

The compounds of the invention may be represented by the structural formula I:

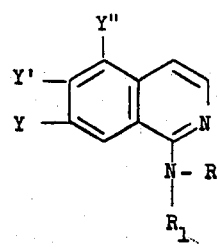

wherein
R is from the group of
a. $-CH_2(-CH_2)_n-ONO_2$ b) $-CH_2(-CH)_n-ONO_2$, with $R°$ on the CH, and c. $-CH_2(-CH_2)_z-N[-CH_2(CH_2)_y-ONO_2]_2$ $R_1$ is from the group of
d. $-CH_2(-CH_2)_n-ONO_2$ when R is (a) as above defined,
e. hydrogen, and
f. lower alkyl of 1 to 4 carbon atoms, $R°$ is hydrogen, $-(CH_2-)_mCH_3$ or $-(CH_2-)_yONO_2$, provided that one $R°$ (and only one) is other than hydrogen, that the sum of n and m does not exceed 6 and that the sum of n and y does not exceed 7, or R and $R_1$ together with the 1- amino nitrogen attached to the isoquinoline ring form

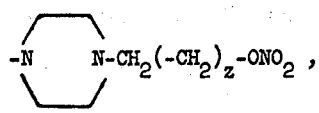

n is 1 to 6, preferably 3 to 5,
m is 0 to 4,
y is 1 to 4,
z is 1 to 4, and
each of Y, Y' and Y'' is hydrogen, lower alkoxy of 1 to 3 carbon atoms, e.g., methoxy or lower alkyl of 1 to 3 carbon atoms, e.g. methyl, or Y and Y' together form methylenedioxy; provided that no more than 2 of Y, Y' and Y'' are lower alkyl; or a pharmaceutically acceptable non-toxic acid addition salt thereof.

A preferred method for preparation of the compounds of formula I involves in a Step A reaction the nitration of the corresponding hydroxy compound of formula II:

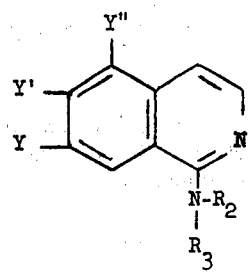

wherein Y, Y' and Y'' are as defined and $R_2$ and $R_3$ are the non-nitrate bearing hydroxyalkyl substituents corresponding to R and $R_1$, respectively, i.e.:

$R_2$ is from the group of:
a. $-CH_2(-CH_2)_n-OH$ b) $-CH_2(-CH)_n-OH$, with $R_a°$ on the CH, and c. $-CH_2(-CH_2)_z-N[-CH_2(-CH_2)_y-OH]_2$ $R_3$ is from the group of:
d. $-CH_2(-CH_2)_n-OH$ when $R_2$ is (a) as above defined,
e. hydrogen, and
f. lower alkyl of 1 to 4 carbon atoms, $R_a°$ is hydrogen, $-(CH_2-)_mCH_3$ or $-(CH_2-)_yOH$, provided that one $R'a°$ is other than hydrogen, that the sum of n and m does not exceed 6 and that the sum of n and y does not exceed 7, or $R_2$ and $R_3$ together with the 1- amino nitrogen attached to the isoquinoline ring form

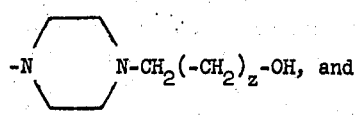

n, m, y and z and Y, Y' and Y'' are as defined.

The preparation of compounds I by Step A involves a nitration reaction which may be carried out in a manner known per se for nitrating hydroxyalkyl groups. A preferred method of conducting the nitration involves the reaction of a compound II with nitric acid in presence of a carboxylic acid anhydride which is preferably of from 3 to 8 carbon atoms, more preferably acetic acid anhydride. The reaction may be suitably carried out in an organic solvent medium at temperatures in the range of from minus 70°C. to plus 50°C., preferably minus 5°C. to plus 20°C. The solvent medium for the reaction is preferably provided by employing a lower aliphatic carboxylic acid, e.g., acetic acid, although other well known organic solvents may be employed or the reaction may be carried out employing an excess of the carboxylic acid anhydride. The product compound I may be isolated from the reaction mixture of Step A by working up by established procedures.

A preferred method for preparation of compounds II involves a Step B reaction of a 1-haloisoquinoline of formula III:

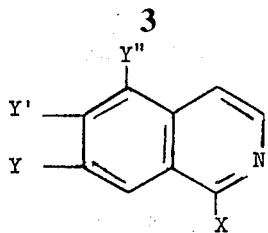

III wherein Y, Y' and Y'' are as defined and X is halo from the group of chloro or bromo, preferably chloro, with a compound of formula IV:

IV wherein $R_2$ and $R_3$ are as defined.

The reaction of Step B is of known type and may be carried out in a conventional manner by subjecting a compound III to reaction with the compound IV at elevated temperatures which may be suitably in the range of 30°C. to 180°C., preferably 60°C. to 160°C. The reaction may be suitably carried out in an inert organic solvent which may be any of several of the well-known conventional solvents, preferably an aromatic solvent such as benzene. Another preferred solvent is isopropanol. Alternately, the reaction may be initiated and/or carried out in the inert liquid medium provided by employing an excess of compound IV when the compound is liquid at the reaction temperature or by fusion of solid reactants. An acid binding agent such as sodium carbonate may be also employed to advantage in the reaction, if desired. The reaction product compound II may be isolated from the reaction mixture of Step B by established procedures.

The compounds of formulae III and IV are either known or may be prepared from known materials by established procedures, for example, as described for compounds III by Anderson et al., J. Am. Pharm. Assoc. Sci. Ed. 41, 643–50 (1952).

Also within the scope of the novel compounds of the invention are pharmaceutically acceptable salts not materially affecting the pharmacological effect of the compounds of formula I. Such salts include the acid addition salts, e.g., the methane sulfonate, hydronitrate, hydrosulfate, fumarate, hydrochloride and maleate. It is convenient to prepare the compounds of formula I as a hydronitrate addition salt. Such salts may be then readily converted to the free bases by conventional procedures. In preparing the free bases from the acid addition salt, it is also convenient to employ a buffer system, e.g., a system comprising a 1:1 molar mixture of acetic acid and sodium acetate, followed by working up by conventional procedures. The free bases may be readily converted into the hydronitrate and other acid addition salts by established procedures.

The compounds of formula I and their pharmaceutically acceptable acid addition salts are useful because they possess pharmacological activity in animals. In particular, the compounds of the formula I, excluding those of the formula Ia as hereinafter defined, are useful as anti-hypertensive agents as indicated by a lowering of blood pressure on intravenous administration to the anesthetized dog in the Cannulated Blood Vessel Test. Such compounds of the formula I (excluding those of the formula Ia) are further useful as antianginal agents as indicated by effecting coronary dilation in the anesthetized dog on intravenous administration and measurement of blood flow through the anterior descending branch of the left coronary artery and by effecting cerebral vasodilation in the anesthetized dog on intravenous administration.

The compounds of the formula I having the formula Ia:

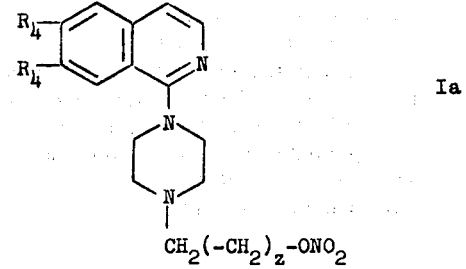

Ia wherein $z$ is as defined and each $R_4$ is lower alkoxy of 1 to 3 carbon atoms, as represented by the compound of Example 1 hereinafter, effect an increase in blood pressure and coronary dilation in the above-identified tests in the anesthetized dog. This unusual and desirable combination of effecting coronary dilation and an increase in blood pressure indicates that the compounds of the formula Ia are useful in the treatment of myocardial or hemorrhagic shock.

For the above uses, the compounds of the formula I including formula Ia may be combined with a pharmaceutically acceptable carrier, and such other conventional adjuvants as may be necessary, and administered orally in such forms as tablets, capsules, elixirs, suspensions and the like or parenterally in the form of an injectable solution or suspension. For the above-mentioned uses, the dosage administered will, of course, vary depending upon the compounds used, the therapy desired and the mode of administration. However, for use as anti-hypertensive agents, satisfactory results in general are obtained with the compounds of the formula I (excluding those of the formula Ia) when administered at a daily dosage of from about 0.2 milligrams to about 100 milligrams per kilogram of body weight, preferably given in divided doses 2 to 4 times a day, or in sustained release form. For most larger mammals, the administration of from about 16 milligrams to about 500 milligrams of the compound per day provides satisfactory results and dosage forms suitable for internal administration comprise from about 4 milligrams to about 250 milligrams of the compound in admixture with a solid or liquid pharmaceutical carrier or diluent.

As anti-anginal agents, satisfactory results may be obtained when administered at a daily dosage of from 0.2 to 100 milligrams per kilogram of body weight, given as required or in divided doses or in sustained release form. For most larger mammals a dosage of from 16 to 500 milligrams, pro re nata, provides satisfactory results. The compounds may also be used prophylactically in mammals to prevent or minimize angina attacks at a daily dosage of 16 to 500 milligrams, or in divided doses of from 4 to 250 milligrams.

For the treatment of myocardial or hemorrhagic shock the compounds of the formula Ia may be administered to obtain effective results at a dosage of from 0.008 to 80 milligrams per kilogram of animal body weight, pro re nata. For most mammals satisfactory results are obtained on the administration of from 0.6 to 200 milligrams, pro re nata. For use in the treatment of such shocks parental administration is usually preferred.

Some of the compounds of the formula II employed as intermediates are known in the art. Various of the compounds of the formula II which are not heretofore known may be represented by the following structural formulae:

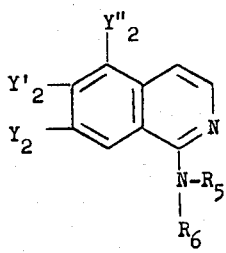

IIa and

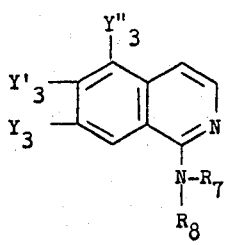

IIb wherein
$R_5$ is $—CH_2(—CH_2)_x—OH$;
$R_6$ is hydrogen or $—CH_2(—CH_2)_n—OH$;
each of
$Y_2$, $Y'_2$ and $Y''_2$ is hydrogen or lower alkoxy of 1 to 3 carbon atoms provided that at least two of $Y_2$, $Y'_2$ and $Y''_2$ are other than hydrogen; or $Y_2$ and $Y'_2$ together form methylenedioxy;
$x$ is 2 to 6;
$R_7$ is from the group of:

a) 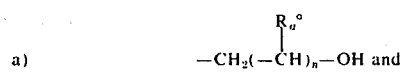

b. $—CH_2(—CH_2)_z—N[—CH_2(CH_2)_y—OH]_2$
$R_8$ is hydrogen, or
$R_7$ and $R_8$ together with the 1-amino nitrogen attached to the isoquinoline ring form

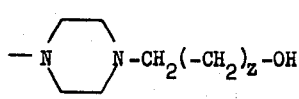

each of
$Y_3$, $Y'_3$ and $Y''_3$ is hydrogen or lower alkoxy of 1 to 3 carbon atoms provided at least one is other than hydrogen, or $Y_3$ and $Y'_3$ together form methylenedioxy, and
$n$, $R_a^o$, $y$ and $z$ are as above defined and subject to the provisos on the sum of $n$ and $m$ and the sum of n and y previously given.

The compounds of the formulae IIa and IIb are also useful as pharmaceutical agents. In particular, the compounds of the formula IIa and IIb, except those of the formula IIc hereinafter, are useful as hypotensive agents as indicated by a lowering of blood pressure in the anesthetized dog on intravenous administration.

The compounds of the formula IIb having the formula IIc:

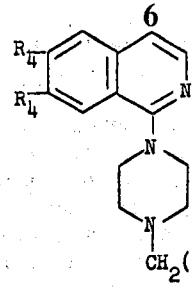

IIc wherein $R_4$ and z are as defined, as represented by the compound of Step A of Example 1 hereinafter, effect coronary dilation and also effect an increase in blood pressure in the anesthetized dog in the above-identified tests for such indications. The compounds of the formula IIc are therefore also useful in the treatment of animals suffering from myocardial or hemorrhagic shock, and for the treatment of such shocks the compounds of the formula IIc are indicated as preferred over those of the formula Ia.

For the use of the compounds of the formulae IIa and IIb (except those of the formula IIc) as hypotensive agents satisfactory results may be obtained when administered at a daily dose of from 0.4 milligram to 150 milligrams per kilogram of body weight. For most mammals the administration of from about 20 to 600 milligrams per day provides satisfactory results and dosage forms comprise from about 5 to 300 milligrams of the compounds in admixture with a solid or liquid carrier or diluent.

For the treatment of myocardial or hemorrhagic shock the compounds of the formula IIc may be effectively administered at a dosage of from 0.004 to 40 milligrams per kilogram of animal body weight, pro re nata. For most mammals satisfactory results are obtained on the administration of from 0.3 to 150 milligrams, pro re nata. For such usage the compounds of the formula IIc are preferably administered parenterally, e.g., intravenously.

The compounds of the formulae IIa and IIb also form acid addition salts and those pharmaceutically acceptable acid addition salts of the compound of the formulae IIa and IIb are included within the scope of the pharmaceutically useful compounds of the formulae IIa and IIb of the invention. Such salts include by way of illustration the hydrochloride, maleate and methanesulfonate and may be formed from or converted to the corresponding free base by conventional procedures.

For the above usages, oral administration with carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, i.e., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan mono-oleate) and preservatives (ethyl-p-hydroxybenzoate). Capsules may contain the active ingredient alone or admixed with an inert solid diluent, e.g., calcium carbonate, calcium phosphate and kaolin. Except for the use in the treatment of shocks the preferred pharmaceutical compositions from the standpoint of preparation and ease of administration are solid compositions, particularly hard-filled gelatin capsules and tablets.

A representative formulation is a tablet prepared by conventional tabletting techniques and containing the following ingredients:

| Ingredients | Weight (mg.) |
| --- | --- |
| Compound of the formula I | 50 |
| Tragacanth | 10 |
| Lactose | 197.5 |
| Corn starch | 25 |
| Talcum | 15 |
| Magnesium stearate | 2.5 |

Compositions for parenteral administration for use, for example, in the treatment of shocks, may be formulated by well-known methods to contain in effective amount of a compound Ia or IIc as active ingredient in a conventional inert carrier or suspension or solvent medium, together with other additives such as dispersing agents, wetting agents, buffering agents and other conventional ingredients, as desired.

A representative formulation for intravenous administration is a solution prepared by standard procedures and containing the following ingredient:

| Ingredient | Weight (%) |
| --- | --- |
| Compound of Step A of Example 1 | 5 |
| Sodium chloride | to make isotonic |
| Buffer Agent | to adjust pH |
| Ethanol, U.S.P. | 10–20 |
| Propylene Glycol | 15–25 |
| Water for Injection | 55–75 |

In general, the compositions of the invention adapted for either oral or parenteral administration may contain 1% to 90% by weight of the active ingredient in combination with the inert carrier, more usually 3% to 40%.

The following examples are given for the purpose of illustration only.

EXAMPLE 1

1-[4-(2-hydroxyethyl)-1-piperazino]-6,7-dimethoxyisoquinoline nitrate dimaleate.

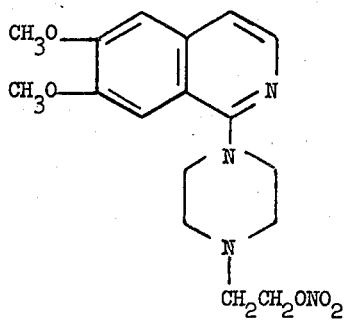

·dimaleate

Step A: Preparation of 1-[4-(2-hydroxyethyl)-1-piperazino]-6,7-dimethoxyisoquinoline A mixture of 2.6 g. of 1-chloro-6,7-dimethoxyisoquinoline and 6.0 g. of 2-hydroxyethylpiperazine is heated at 140°C. for 2 hours and then combined with 50 ml. of isopropanol and 2 g. of sodium carbonate. The resulting mixture is refluxed for 15 minutes, filtered, evaporated in vacuo to an oil which is purified by chromatography on silica gel to obtain 1-[4-(2-hydroxyethyl)-1-piperazino]-6,7-dimethoxyisoquinoline, m.p. 115°–118°C.

Step B: Preparation of 1-[4-(2-hydroxyethyl)-1-piperazino]-6,7-dimethoxyisoquinoline nitrate dimaleate A solution of 2.37 g. of 1-[4-(2-hydroxyethyl)-1-piperazino]-6,7-dimethoxyisoquinoline in 12 ml. of acetic acid is added dropwise to a stirred mixture of 4.3 ml. of acetic anhydride and 1.4 ml. of 90% nitric acid at a temperature of 5°C. The resulting mixture is stirred for 10 minutes and then added to an excess of ice-cold aqueous ammonia solution. The resulting mixture is extracted with methylene chloride and the extract dried and evaporated in vacuo to an oil which is purified by chromatography on silica gel to obtain an amber oil of the free base of the title compound. This oil in an amount of 1.35 g. is dissolved in methylene chloride and 0.855 g. of maleic acid added. The resulting solution is filtered, evaporated to a small volume and the residue crystallized from methanol/diethyl ether to obtain 1-[4-(2-hydroxyethyl)-1-piperazino]-6,7-dimethoxyisoquinoline nitrate dimaleate, m.p. 139°C. (decomp.).

EXAMPLE 2

1-(5-hydroxypentyl)amino-6,7-methylenedioxyisoquinoline nitrate maleate.

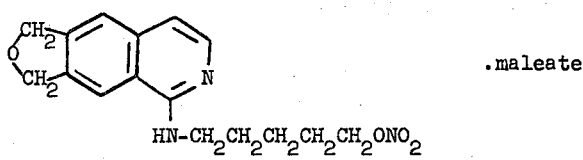

·maleate

Step A: Preparation of 1-(5-hydroxypentyl)amino-6,7-methylenedioxy-isoquinoline

A mixture of 1.8 g. of 1-chloro-6,7-methylenedioxyisoquinoline and 5 g. of 5-hydroxypentylamine is heated at 140°C. for 5.5 hours. The resulting material is dissolved in methanol, sodium carbonate added and the resulting mixture refluxed for 15 minutes. The resulting mixture is filtered and evaporated in vacuo to an oil which is dissolved in chloroform. The resulting solution is evaporated in vacuo and the residue purified by chromatography over silica gel. The resulting oily product is then crystallized from ethanol/ethyl acetate and recrystallized from ethyl acetate/methanol to obtain 1-(5-hydroxypentyl)amino-6,7-methylenedioxyisoquinoline, m.p. 132.5°–134°C.

Step B: Preparation of 1-(5-hydroxypentyl)amino-6,7-methylenedioxyisoquinoline nitrate maleate A solution of 0.835 g. of 1-(5-hydroxypentyl)amino-6,7-methylenedioxyisoquinoline and 1 ml. of acetic acid is added dropwise to a stirred mixture of 1.32 ml. of acetic anhydride and 0.44 ml. of nitric acid at a temperature of minus 3°C. The reaction mixture is stirred for about 20 minutes at about minus 3°C., and then added to an excess of ice-cold aqueous ammonia solution and twice extracted with ethyl acetate. The combined organic extracts are dried, filtered and evaporated in vacuo to an oil which is redissolved in chloroform. The resulting solution is passed through silica gel to obtain 0.965 g. of an oil of the free base of the above title compound. This oil is dissolved in methylene chloride and 0.5 g. of maleic acid is added. The resulting solution is filtered, evaporated to a small volume and diethyl ether added to crystallize a material which is then recrystallized from methanol/diethyl ether to obtain 1-(5-hydroxypentyl)amino-6,7-methylenedioxyisoquinoline nitrate maleate, m.p. 138°–139.5°C.

EXAMPLE 3

Following the procedure of Example 2 the following compounds are similarly prepared:

a. 1-[3-bis(2-hydroxyethyl)aminopropyl]amino-6,7-dimethoxyisoquinoline.

a-1. 1-[3-bis(2-hydroxyethyl)aminopropyl]amino-6,7-dimethoxyisoquinoline dinitrate dimaleate, m.p. 81°C. (decomp.).

b. 1-[3-bis(2-hydroxyethyl)aminopropyl]amino-6,7-methylenedioxyisoquinoline. (recrystallized from ethanol).

b-1. 1-[3-bis(2-hydroxyethyl)aminopropyl]amino-6,7-methylenedioxyisoquinoline dinitrate dimaleate, as an oil.

c. 1-[4-(2-hydroxyethyl)-1-piperazino]-6,7-methylenedioxyisoquinoline.

c-1. 1-[4-(2-hydroxyethyl)-1-piperazino]-6,7-methylenedioxyisoquinoline nitrate dimaleate, m.p. 139°C. (decomp.). (crystallized from methanol/diethyl ether).

d. 1-[3-bis(2-hydroxyethyl)aminopropyl]aminoisoquinoline.

d-1. 1-[3-bis(2-hydroxyethyl)aminopropyl]aminoisoquinoline dinitrate dihydrochloride, m.p. 123.5°–126°C. (decomp.). (crystallized from methanol/isopropanol/diethyl ether).

e. 1-[4-(2-hydroxyethyl-1-piperazino]-isoquinoline.

e-1. 1-[4-(2-hydroxyethyl)-1-piperazino]-isoquinoline nitrate dihydrochloride, m.p. 173°C. (decomp.).

f. 1-(5-hydroxypentyl)amino-isoquinoline, m.p. 109°–110°C. (crystallized from ethyl acetate).

f-1. 1-(5-hydroxypentyl)amino-isoquinoline nitrate hydronitrate, m.p. 121°–122°C. (decomp.) (crystallized from methanol/ diethyl ether).

What is claimed is:

1. A compound of the formula:

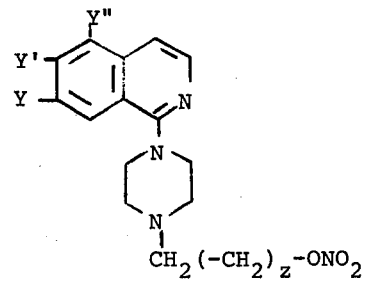

wherein z is 1 to 4 and each of Y, Y' and Y'' is hydrogen, alkoxy of 1 to 3 carbon atoms or alkyl of 1 to 3 carbon atoms, or Y and Y' together form methylenedioxy; provided that no more than 2 of Y, Y' and Y'' are lower alkyl; or a pharmaceutically acceptable non-toxic acid addition salt thereof.

2. A compound of claim 1 having the formula:

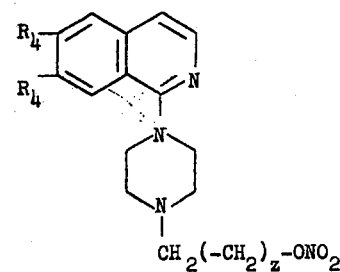

in which each $R_4$ is alkoxy and z is 1 to 4, or a pharmaceutically acceptable non-toxic acid addition salt thereof.

3. The compound of claim 2 in which each $R_4$ is methoxy and z is 1.

4. The compound of claim 3 in the form of a pharmaceutically acceptable non-toxic acid addition salt thereof.

5. The compound of claim 1 in which Y'' is hydrogen, Y and Y' together form methylenedioxy and z is 1.

6. The compound of claim 1 in which each of Y, Y' and Y'' is hydrogen and z is 1.

* * * * *